(12) United States Patent
Hayman

(10) Patent No.: US 10,909,879 B1
(45) Date of Patent: *Feb. 2, 2021

(54) MULTILINGUAL INTERFACE FOR THREE-STEP PROCESS FOR MIMICKING PLASTIC SURGERY RESULTS

(71) Applicant: Hillary Hayman, Los Angeles, CA (US)

(72) Inventor: Hillary Hayman, Los Angeles, CA (US)

(73) Assignee: Elyse Enterprises LLC, Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/931,252

(22) Filed: Jul. 16, 2020

(51) Int. Cl.
*G09B 19/00* (2006.01)
*G06F 3/16* (2006.01)
(Continued)

(52) U.S. Cl.
CPC ....... *G09B 19/003* (2013.01); *A61M 37/0015* (2013.01); *G06F 3/0482* (2013.01);
(Continued)

(58) Field of Classification Search
CPC .... G06F 9/454; G06F 19/34; A61M 37/0015; A61M 2037/0061
See application file for complete search history.

(56) References Cited

U.S. PATENT DOCUMENTS 5,583,761 A * 12/1996 Chou ...................... G06F 9/454
715/201
6,559,861 B1 * 5/2003 Kennelly ................ G06F 9/454
715/703
(Continued)

FOREIGN PATENT DOCUMENTS

JP 2019511343 4/2019

OTHER PUBLICATIONS

Westofwild. "A Powerful Anti-Aging Ritual You Can Do At Home." https://www.wowpublication.com/2020/03/anti-aging-skincare-ritual-at-home/. Mar. 20, 2020. (Year: 2020).*
(Continued)

*Primary Examiner* — Shaun Roberts
(74) *Attorney, Agent, or Firm* — Patent Ingenuity, P.C.; Samuel K. Simpson

(57) ABSTRACT

A computer program product comprises a non-transitory computer readable storage that has a computer readable program stored thereon. When executed on a computer, the computer readable program causes the computer to select, with a processor, a multilingual graphical user interface template corresponding to a three-step skincare treatment process. The multilingual graphical user interface template has a layout of all of the objects present in a multilingual graphical user interface without any content displaying a human-spoken language. Furthermore, the computer is caused to determine, with the processor, a preferred spoken language of a user operating a computing device. Additionally, the computer is caused to automatically select, from a multilingual object database, one or more audiovisual objects composed in the preferred spoken language and one or more menu objects composed in the preferred spoken language.

19 Claims, 9 Drawing Sheets

(51) Int. Cl.
*G06F 3/0484* (2013.01)
*A61M 37/00* (2006.01)
*G09B 5/06* (2006.01)
*G16H 20/40* (2018.01)
*G06F 9/451* (2018.01)
*G06F 3/0482* (2013.01)

(52) U.S. Cl.
CPC ............ *G06F 3/0484* (2013.01); *G06F 3/167* (2013.01); *G06F 9/454* (2018.02); *G09B 5/065* (2013.01); *G16H 20/40* (2018.01)

(56) References Cited

U.S. PATENT DOCUMENTS

| | | |
|---|---|---|
| 8,376,984 B2 | 2/2013 | James |
| 9,144,434 B1 | 9/2015 | Rodan et al. |
| 2002/0133523 A1* | 9/2002 | Ambler .................. G06F 9/454 715/265 |
| 2004/0085570 A1* | 5/2004 | Sfaelos .................. G06F 9/454 358/1.15 |
| 2004/0191330 A1* | 9/2004 | Keefe .................... A61K 36/30 424/638 |
| 2006/0167677 A1* | 7/2006 | Bitzer .................... G06F 9/454 704/9 |
| 2007/0073217 A1 | 3/2007 | James |
| 2007/0124675 A1* | 5/2007 | Ban ........................ G06F 9/454 715/703 |
| 2008/0161661 A1* | 7/2008 | Gizewski ............ G06F 19/3418 600/306 |
| 2008/0300518 A1 | 12/2008 | Bowes |
| 2009/0118698 A1 | 5/2009 | Liebl |
| 2010/0045427 A1 | 2/2010 | Boone, III et al. |
| 2010/0185064 A1* | 7/2010 | Bandic .................. G16H 50/20 600/306 |
| 2011/0040236 A1 | 2/2011 | Isaacs et al. |
| 2011/0040571 A1* | 2/2011 | Warren .................. G06Q 10/00 705/2 |
| 2011/0301441 A1* | 12/2011 | Bandic .................. A61B 5/442 600/306 |
| 2012/0010886 A1 | 1/2012 | Razavilar |
| 2013/0150878 A1 | 6/2013 | Church |
| 2014/0297258 A1* | 10/2014 | Kiss ........................ G06F 9/454 704/8 |
| 2015/0005326 A1 | 1/2015 | Jang et al. |
| 2015/0065950 A1 | 3/2015 | Banar |
| 2015/0231382 A1 | 8/2015 | Altarac |
| 2015/0347394 A1* | 12/2015 | Hirama .................... G06F 8/38 715/703 |
| 2015/0347396 A1* | 12/2015 | Goldberger ........... G01M 99/00 704/3 |
| 2016/0135889 A1 | 5/2016 | Serrano Sanmiguel et al. |
| 2016/0335910 A1 | 11/2016 | Baumann |
| 2017/0340267 A1* | 11/2017 | Shen ...................... A61B 5/749 |
| 2018/0071547 A1 | 3/2018 | Decaux et al. |
| 2018/0185196 A1 | 7/2018 | Levinson et al. |
| 2019/0091113 A1 | 3/2019 | Danto |
| 2019/0387930 A1 | 12/2019 | Fauconnier |
| 2020/0121354 A1 | 4/2020 | Ginggen et al. |
| 2020/0246039 A1 | 8/2020 | Levinson et al. |

OTHER PUBLICATIONS

International Search Authority, International Search Report and Written Opinion for PCT/US20/42662, dated Sep. 30, 2020.
Martanto, W., et al. "Microinfusion Using Hollow Microneedles," Pharmaceutical Research, vol. 23, No. 1, pp. 104-113, Jan. 2006.
Spiegel, J., "How Creams with Caffeine Can Help Your Skin," https://www.drspiegel.com/skin-care/how-creams-with-caffeine-can-help-your-skin/, Oct. 8, 2015.
Gallagher, G., "The Benefits of a Face Roller," https://www.healthline.com/health/face-roller-benefits, Jan. 31, 2020.
International Search Authority, International Search Report and Written Opinion for PCT/US20/42603, dated Oct. 15, 2020.
Singh, A., et al., "Microneedling: Advances and Widening Horizons," Indian Dermatology Online Journal, https://www.ncbi.nlm.nih.gov/pmc/articles/PMC4976400/, pp. 1-21, Jul.-Aug. 2016.
Youyaner, "How to Choose the Best Derma Roller Needle Size," http://dermarollerinfo.com/derma-roller-needle-size/, pp. 1-4, Feb. 6, 2020.
International Search Authority, International Search Report and Written Opinion for PCT/US20/42655, dated Nov. 6, 2020.

* cited by examiner

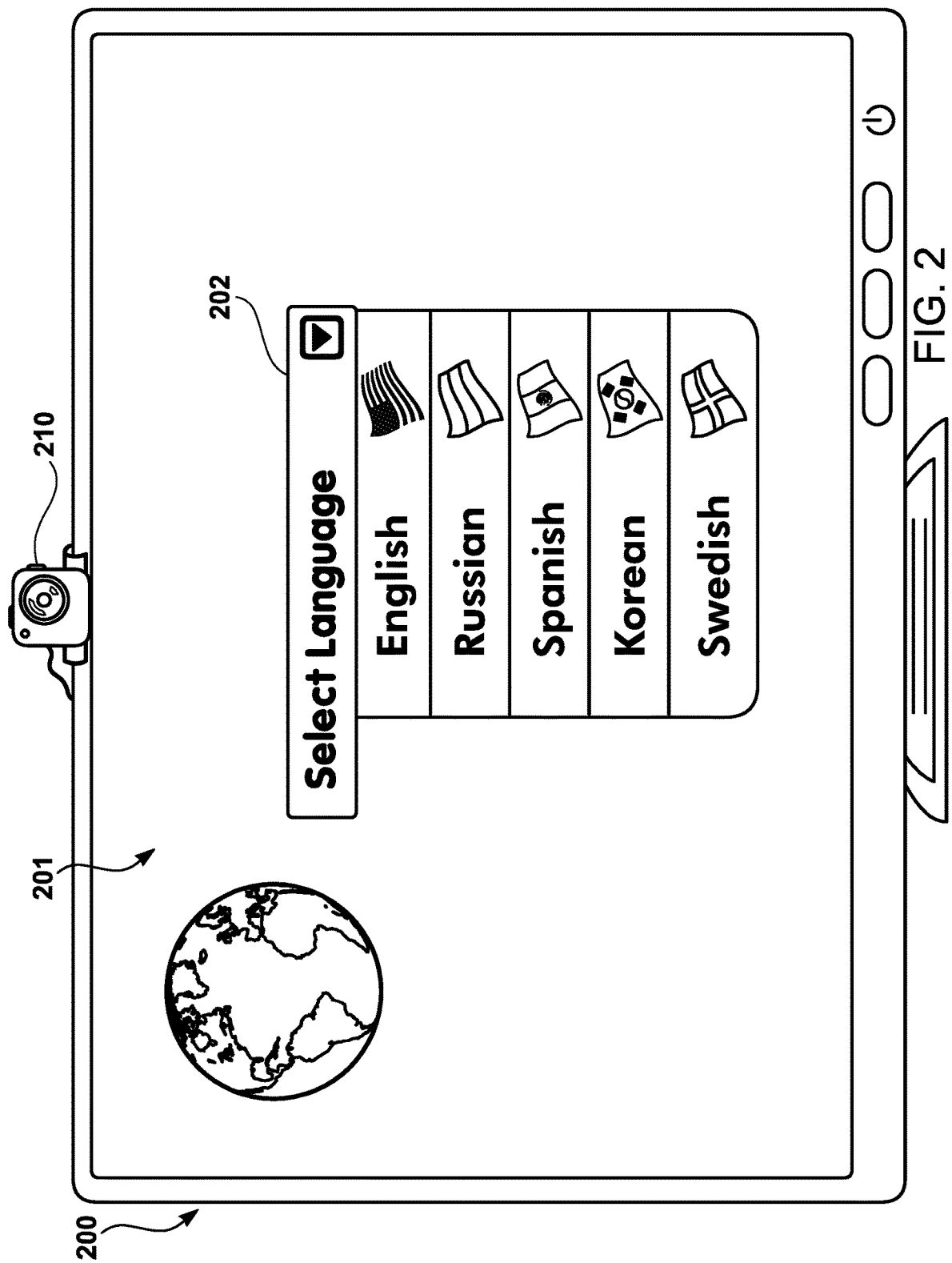

MULTILINGUAL INTERFACE FOR THREE-STEP PROCESS FOR MIMICKING PLASTIC SURGERY RESULTS

BACKGROUND

1. Field

This disclosure generally relates to skincare processes. More particularly, the disclosure relates to a computer-implemented user interface for a process that mimics plastic surgery results.

2. General Background

A plastic surgery procedure is typically performed in an office of a plastic surgeon, often at significant expense and inconvenience for those people wanting to improve the appearance of their skin. For instance, many people often have to travel far distances to obtain the services of a qualified plastic surgeon to perform the plastic surgery procedure. Although some people may elect to have a plastic surgery procedure (e.g., facelift, jaw lift, eye wrinkle reduction, etc.) to rejuvenate the appearance of their skin, others require plastic surgery to diminish or eliminate the effects (e.g., scar tissue reduction, burn minimization, etc.) from injuries. As a result, plastic surgery procedures are typically accessible only to a limited group, which may exclude those who need them most.

Furthermore, even when people undergo plastic surgery procedures, risks are associated therewith. In some instances, those undergoing plastic surgery procedures may end up with significant disfiguration. Although the skill and experience of the plastic surgeon may play a part, other factors, such as the way the skin heals for different people, may also lead to potential disfiguration. Ultimately, plastic surgery procedures often involve significant levels of invasiveness that may injure the skin of the user.

Yet, alternative, non-invasive approaches have had questionable, if any, efficacy. For example, one alternative approach utilizes micro current technology to stimulate adenosine triphosphate ("ATP") production in an attempt to create collagen and elastin to provide a lifted appearance of the skin. However, this approach appears to have results that do not mirror plastic surgery results. Another approach may utilize radio frequency ("RF") emissions in conjunction with micro current emissions, but this approach may lead to results that worsen the skin, such as excessive redness. Yet another approach purports to oxygenate the skin to improve blood flow, but has led to health concerns, such as a racing heart, chest pressure, and light headedness.

Accordingly, current skincare configurations suffer from procedures that are too invasive (i.e., plastic surgery procedures that are costly, inconvenient, and vulnerable to possible disfiguration) or too non-invasive (i.e., devices that solely rely on technologies that emit electricity, radio waves, air, or the like above the surface of the skin of a person).

SUMMARY

In one embodiment, a computer program product comprises a non-transitory computer readable storage that has a computer readable program stored thereon. When executed on a computer, the computer readable program causes the computer to select, with a processor, a multilingual graphical user interface ("GUI") template corresponding to a three-step skincare treatment process. The multilingual GUI template has a layout of all of the objects present in a multilingual GUI without any content displaying a human-spoken language. Furthermore, the computer is caused to determine, with the processor, a preferred spoken language of a user operating a computing device. Additionally, the computer is caused to automatically select, from a multilingual object database, one or more audiovisual objects composed in the preferred spoken language and one or more menu objects composed in the preferred spoken language. Finally, the computer is caused to automatically generate, with the processor, the multilingual GUI by populating the multilingual GUI template with the one or more audiovisual objects composed in the preferred spoken language and the one or more menu objects composed in the preferred spoken language. The multilingual GUI is configured to render audiovisual content associated with a three-step skincare treatment process.

The three-step skincare treatment process includes a first step for performing, with a derma roller, a plurality of movements along an area of intended rejuvenation of a human user. Furthermore, a second step applies, subsequent to the derma roller performance, a chemical compound to one or more patches of skin at the area of intended rejuvenation. Finally, a third step emits, subsequent to the application of the chemical compound, light toward the area of intended rejuvenation. The three-step process may be customized to a user based on a variety of factors (e.g., area of intended rejuvenation, age, skin sensitivity, or the like).

BRIEF DESCRIPTION OF THE DRAWINGS

The above-mentioned features of the present disclosure will become more apparent with reference to the following description taken in conjunction with the accompanying drawings wherein like reference numerals denote like elements and in which:

FIG. 2 illustrates a display device that renders an introductory screen of a multilingual GUI, which may be rendered on a variety of different virtual platforms, such as websites, software applications, social media outlets, etc.

DETAILED DESCRIPTION

Figure 1:
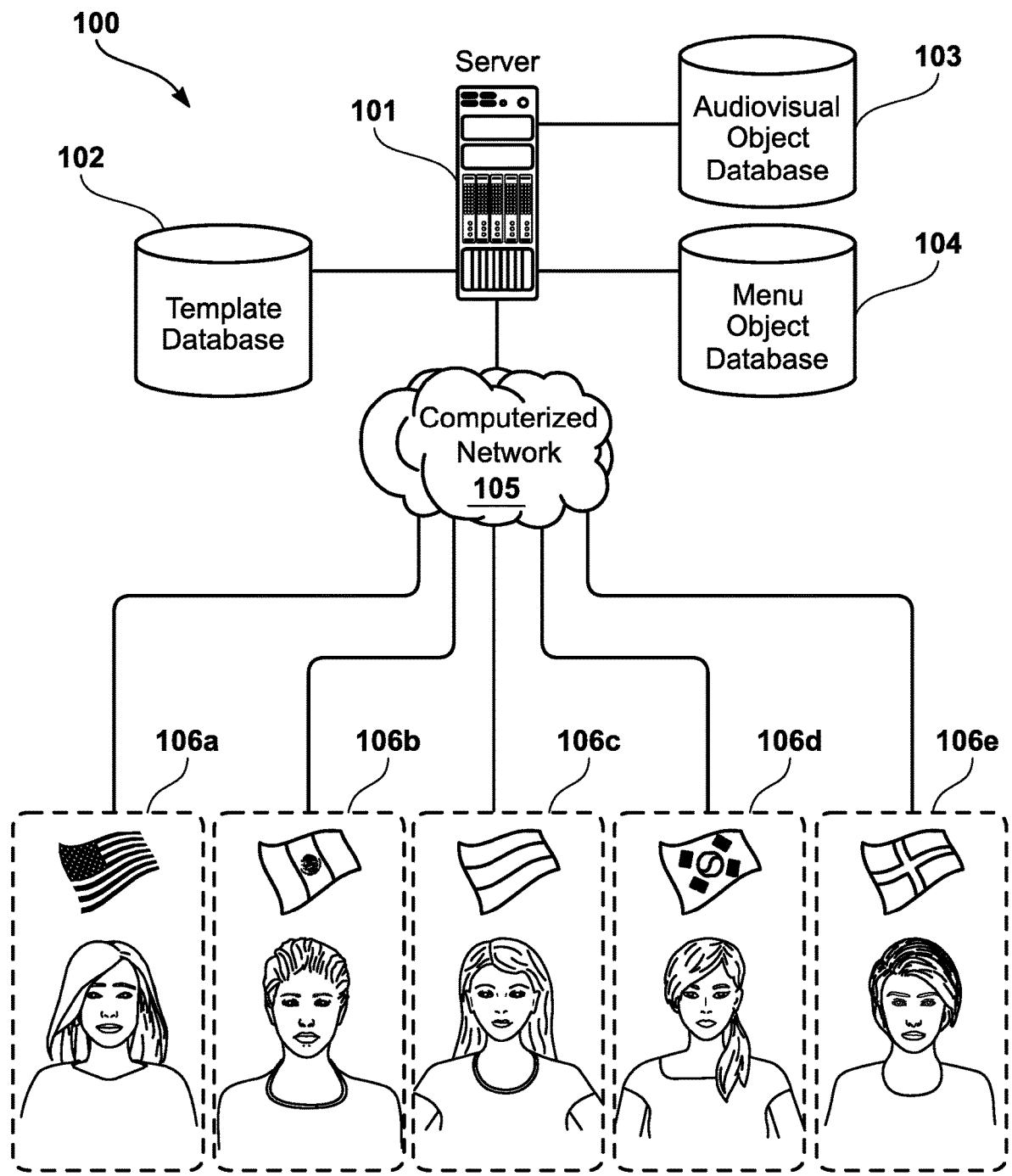
FIG. 1 illustrates a multilingual content generation system for generating a graphical user interface ("GUI") that provides accessibility to content associated with a three-step skincare treatment process.

A computer-implemented multilingual GUI is provided to electronically deliver a three-step skincare treatment process to users in a plurality of different human-spoken languages via a variety of different virtual platforms. (A human-spoken language is traditionally spoken by a group of people originating from a particular geographical location, country, or region.) The three-step skin treatment process provides users with skincare rejuvenation that mimics plastic surgery results, without users having to undergo conventional plastic surgery procedures within a plastic surgeon's office. By way of contrast, the three-step skin treatment process may be performed from the convenience of one's own home, or other place of comfort.

To avoid language barriers, the computer-implemented GUI adapts the content of the virtual platforms viewed by a user, who is using the three-step skincare treatment process, to reflect the human-spoken language that is spoken by a particular user. The audiovisual content (e.g., videos providing guidance for using the three-step skincare treatment process), menus, product offerings, and/or advertisements may be displayed in the human-spoken language of the user. In one embodiment, the computer-implemented multilingual GUI renders such user-specific content after selection by a multilingual processor of applicable content from a content database. In other words, after a determination of the specific human-spoken language of the user, the multilingual processor selects the content (e.g., webpages, menu text, product descriptions, etc.) corresponding to the human-spoken language, and renders that content for the user. As opposed to having subtitles, voice-overs, or the like, which diminish the overall user experience, the computer-implemented multilingual GUI has content specifically produced for each particular human-spoken language, thereby providing an authentic user experience for each user in his or her respective human-spoken language.

In particular, the three-step process has been discovered to yield results that were not readily predictable; such results mimic the effects of various plastic surgery procedures (e.g., facelifts, jaw lifts, neck lifts, forehead lifts, lower eyelid blepharoplasty, and the like) without a user having to undergo a plastic surgery procedure at the office of a medical practitioner. In essence, the three-step process includes application of various invasive and non-invasive devices/products according to particular parameters to mimic plastic surgery results. Firstly, the three-step process includes usage of a derma roller in an area of intended rejuvenation. Particular needle lengths and movements of the derma roller have been discovered to maximize skin rejuvenation. Secondly, a chemical compound containing vitamin $A_1$ (e.g., Retinol) is applied to the area of intended skin rejuvenation via the channels in the skin created by the derma roller. Accordingly, the chemical compound is able to reach the dermis layer of the skin, directly underneath the epidermis, much faster than would be required through prolonged exposure to the chemical compound; as a result, collagen production is increased in an optimal manner to rejuvenate (i.e., tone, tighten, and/or lift) the skin. Finally, a red light therapy device is utilized to emit red light (i.e., light having a wavelength of six hundred ten nanometers to seven hundred nanometers) toward the area of intended rejuvenation, which further increases collagen production.

Accordingly, the positioning of the chemical compound within the channels created by derma roller, combined with the sequential step of red light emission toward the area of intended rejuvenation, has been discovered to have an enhanced collagen production effect that mimics plastic surgery results.

Furthermore, the same three-step process may be utilized in a universal manner with respect to various portions of the face to mimic plastic surgery results corresponding to different plastic surgery procedures (e.g., face lift, jaw lift, etc.), but with the same process. In other words, one process may be utilized in different zones of the face of a user to mimic plastic surgery results that would typically require different plastic surgery procedures, associated with potentially different visits to a plastic surgeon's office.

Moreover, in one embodiment, the three-step process may be utilized to simultaneously mimic the results from multiple plastic surgery procedures during one application. For example, the user may apply the derma roller to both the skin around the eyes and the skin around the jaw during one application, followed by application of retinol to the skin around the eyes and the skin around the jaw, and followed by red light therapy emission to the skin around the eyes and the skin around the jaw. Accordingly, the three-step process allows a user to simultaneously mimic plastic surgery results corresponding to multiple plastic surgery procedures at the same time, and by using the same process, without necessitating any variation thereto.

FIG. 1 illustrates a multilingual content generation system 100 for generating a GUI that provides accessibility to content associated with the three-step skincare treatment process. The multilingual content generation system 100 has a multilingual server 101 that accesses various audiovisual content (e.g., instructional videos) from an audiovisual object database 103 and menu content from a menu object database 104 based on a determination of a human-spoken language that is spoken by a user. The server 101 may be in operable communication with a template database 102 that stores a multilingual GUI template, and may retrieve audiovisual content from the audiovisual object database 103 and menu content from the menu object database 104 to automatically populate the multilingual GUI template with the videos and menu items corresponding to the preferred spoken language. Accordingly, instead of storing a full page of content for preferred spoken language, which would include multiple redundancies, the server 101 utilizes a multilingual GUI template that has all duplicative data, without specific language data. Thus, the layout of the multilingual GUI may be established by the multilingual GUI template to avoid redundancies in storing duplicative layout data for each language-specific version of a virtual platform, which would otherwise be numerous and reduce processing speeds. By diminishing memory requirements via use of the multilingual GUI template, the multilingual server 101 is able to improve processing speeds by using a specialized multilingual processor to provide real-time (measured as an imperceptible time delay), or substantially real-time (measured as a perceptible time delay that is generally acceptable to the user (e.g., one to two seconds)), access to audiovisual content associated with the three-step skincare treatment process in the preferred spoken language of the user.

In another embodiment, a content database stores multiple full versions of the multilingual GUI with layouts that have redundancies. The multilingual server 101 may select the content that corresponds most to the preferred spoken language of the user.

To determine the preferred spoken language of the user, the multilingual server 101 may receive geographical positioning data specific to a particular user (i.e., from a global positioning system ("GPS")), such as that emanating from a computing device operated by the user, and automatically selects content for the user experience provided by the virtual platforms based on the corresponding human-spoken language. For example, a plurality of users 106a-e may be geographically situated in various countries, and the GPS, or other location-based detection system, may be utilized to determine such geographic areas based on location-based data sent from respective computing devices (e.g., personal computer, laptop, smartphone, tablet device, smartwatch, etc.) to the server 101 through a computerized network 105. (Different numbers of users and different countries than those illustrated may be utilized. The depictions in FIG. 1 are provided only as examples.) However, a human-spoken language that is typically spoken by people that live in the same geographical region as a user is not always the preferred spoken language for that user. Accordingly, in another embodiment, the multilingual content generation system 100 may invoke an onboarding process that displays an introductory screen that asks the user his or her preferred language. The introductory screen may be initiated in the language determined based on the geographical region of the user, which may be automatically determined, such as via a GPS, or manually inputted by the user. If the user wants to proceed in a different language than that which is typically spoken in the identified region in which he or she is operating a computing device, the user may provide a user input indicating the different language. Alternatively, the multilingual server 101 may determine the preferred spoken language of the user solely on a manual input of the user, without any location-based determination.

As an example, FIG. 2 illustrates a display device 200 that renders an introductory screen of a multilingual GUI 201, which may be rendered on a variety of different virtual platforms, such as websites, software applications, social media outlets, etc. In particular, the introductory screen has a language selection menu 202, which allows a user to select his or her preferred spoken language. For example, FIG. 2 illustrates the language selection menu 202 being a drop-down menu from which one of a plurality of languages (e.g., English, Russian, Spanish, Japanese, and Swedish) may be selected for use with the three-step skincare treatment process content displayed by the corresponding virtual platform. (The languages depicted by the language selection menu 202 are provided only as examples, given that a variety of other languages may be provided for in the language selection menu 202.)

The display device 200 is illustrated as a computer monitor, as an example; however, the display device 200 may be a variety of other types of display devices, which may or may not be integrated within a computing device (e.g., personal computer, laptop computer, smartphone, tablet device, smartwatch, or the like). Optionally, an image capture device 210 may be in operable communication with, or integrated within, the display device 200. The image capture device 210 may capture imagery of the user for display on the display device 200 operated by the user, and potentially a display device of a human practitioner of the three-step skincare treatment process that may provide guidance to the user regarding the three-step skincare treatment process.

Figure 3A:
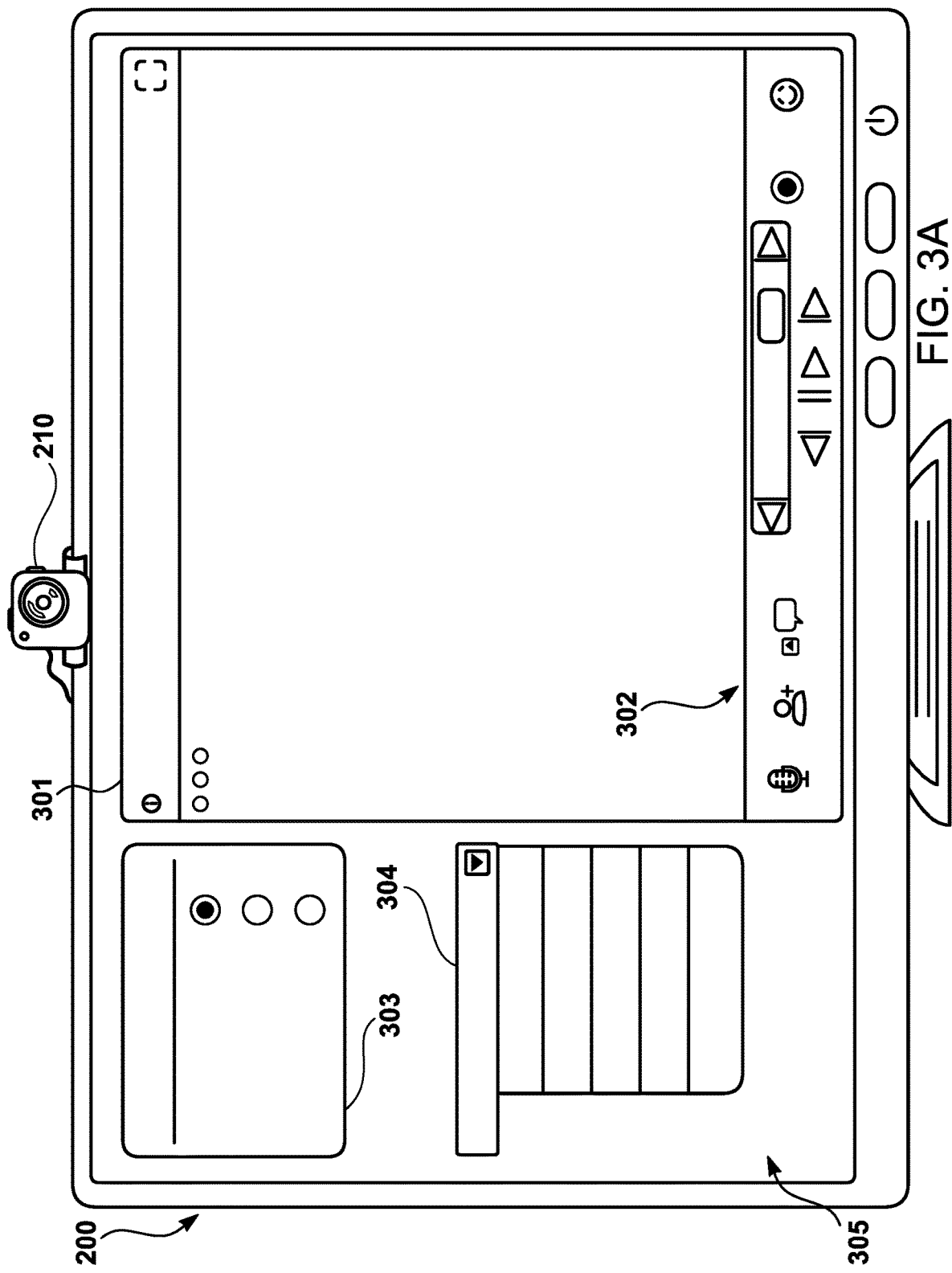
FIG. 3A illustrates multilingual graphical user interface template, which essentially has a common layout without language-specific text.

FIGS. 3A-3D illustrate the display device 200 displaying one or more templates and GUIs for utilization with the three-step skincare treatment process. In particular, FIG. 3A illustrates a multilingual graphical user interface template 305, which essentially has a common layout without language-specific text. Accordingly, the multilingual GUI template 305 has a plurality of layout containers, which may be populated with language specific objects upon a determination of a preferred language of a user of the three-step skincare treatment process operating the display device 200. For instance, the multilingual GUI template 305 may have an audiovisual container 301 in which an audiovisual object may be placed for playback of an instructional video corresponding to three-step skincare treatment process, and a control menu container 302 in which various controls may be activated to control playback of the instructional video. Given that the audiovisual content may change from video to video, the audiovisual container 301 is empty. However, the control menu container 302 may have various images (e.g., images for playback, rewind, fast forward, chat, etc.), without the corresponding language-specific text, that may be present irrespective of which language is selected as the preferred language for the user.

Additionally, the multilingual GUI template 305 may have a product/kit selection menu container 303 and an area of intended skincare rejuvenation container 304, each of which may be populated with corresponding menu items upon a determination of the preferred spoken language of the user.

The multilingual GUI template 305 is depicted to illustrate template components prior to automatic population of language-specific content; however, in one embodiment, the user may not view the multilingual GUI template 305. Instead, the user may view the multilingual GUI 201 after automatic population. In other words, the user may be insulated from viewing the mechanics of how the multilingual GUI is generated.

Figure 3B:
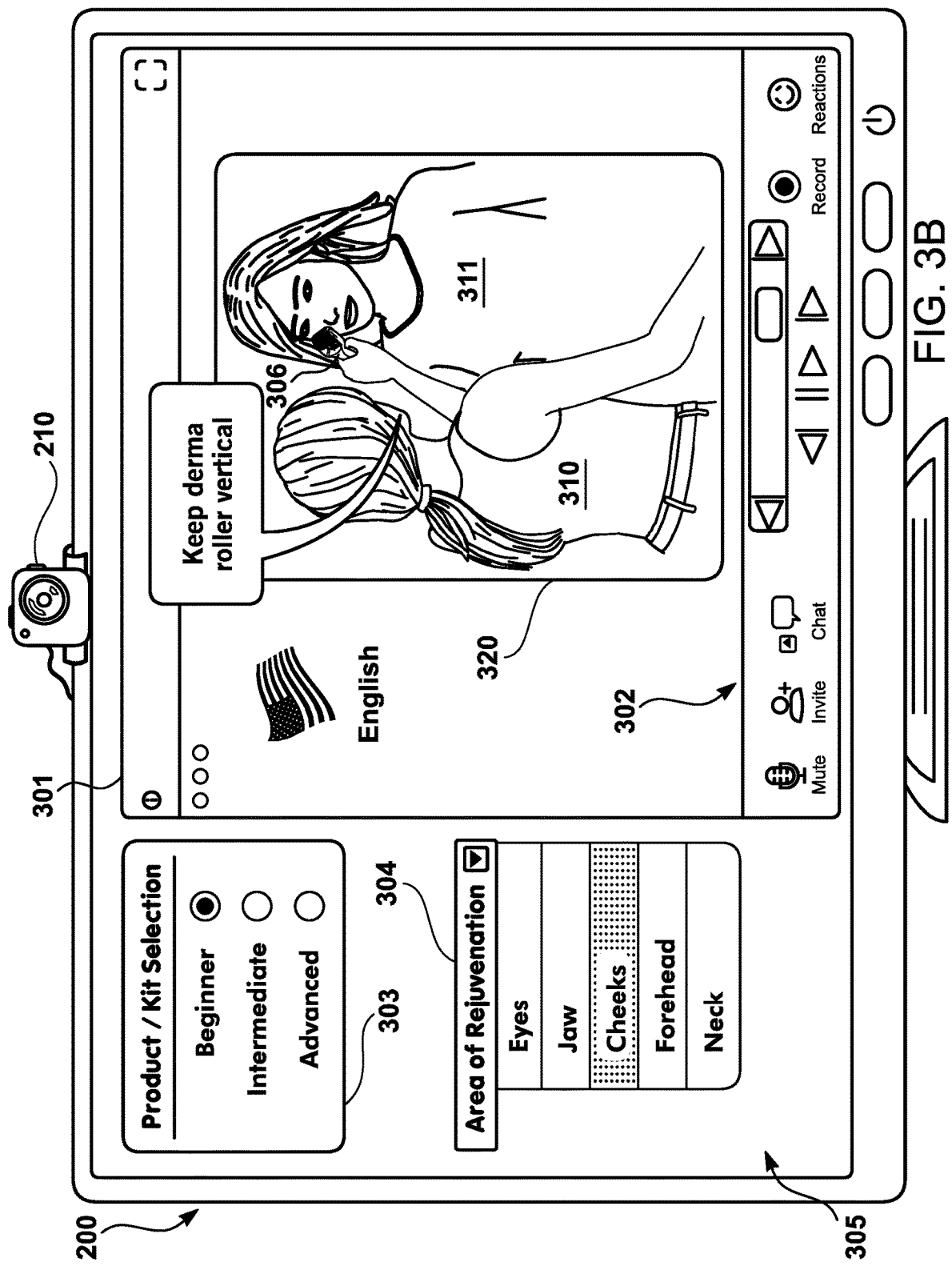
FIG. 3B illustrates an example of the multilingual GUI, which is either the result of automatically populating the multilingual GUI template with English-specific content or selecting an English-specific version of content with template population.

FIG. 3B illustrates an example of the multilingual GUI 201, which is either the result of automatically populating the multilingual GUI template 305 with English-specific content or selecting an English-specific version of content. In particular, FIG. 3B illustrates an audiovisual window 320 that depicts an English-specific window corresponding to the first step of the three-step skincare treatment process. A virtual demonstrator 310 (human or computer generated) is illustrated to demonstrate usage of a derma roller 306 on a virtual demonstration participant 311 (human or computer generated). The demonstration is vocalized by the virtual demonstrator 310 of the first step of the three-step skincare treatment process in English, given that the user of the display device 200 was determined to have an English language preference. To provide the most convenient user experience, the multilingual content generation system 100 may provide not only audio-emission based content in the preferred language of the user, but also text-based content displayed through the multilingual GUI 201 as well. For example, the text associated with the imagery in the control menu container 302 is specified in English. Furthermore, the text in the product/kit selection menu container 303 and the area of intended skincare rejuvenation container 304 also may be displayed in English.

The product/kit menu allows the user to provide a user input to select the particular product or kit for which the user wishes to obtain audiovisual content. Alternatively, or in addition, the product/kit menu may have skincare rejuvenation level menu selections (e.g., beginner, intermediate, and advanced) from which the user may select a skincare rejuvenation level that corresponds to the user's current level of the three-step skincare treatment process. In other words, the three-step skincare treatment process is adapted via various parameters (e.g., needle lengths, chemical compound potencies, red light emission exposure times, etc.) to the current skincare rejuvenation level of a user.

Additionally, the area of skincare rejuvenation menu allows the user to select the particular part of the skin (e.g., skin around the eyes, jaw, cheeks, forehead, neck, etc.) that is intended to be rejuvenated. The parameters of the three-step process may also be adapted based on the intended area of rejuvenation. For example, certain areas with thicker skin (e.g., stomach) than others (e.g., face) may have corresponding parameters, such as longer needle lengths.

During the first step of the three-step skincare treatment process, the virtual demonstrator 310 illustrates how to utilize a derma roller 306 in the particular manner specific to the three-step skincare treatment process. As an example, the virtual demonstrator 310 may be a daughter that is demonstrating the three-step process on a demonstration participant 311, who is her mother. (This example is provided only for illustration purposes. Different types and numbers of demonstrators and/or demonstration participants may be utilized.) In particular, the virtual demonstrator 310 of the three-step process is illustrated as utilizing a derma roller 306 on the face of the skin of the demonstration participant 311. The virtual demonstrator 310 of the three-step process explains how to use the derma roller 306 most effectively on the demonstration participant 311 for the first step of the three-step process, based on a variety of factors. One factor may be the skincare rejuvenation level of the user selected by the user in the product/kit menu, which corresponds to the product or kit currently being utilized by the user. Other factors may include, but are not limited to, age, skin type, skin sensitivity, etc. Based on these various factors, the virtual demonstrator 310 of the three-step process may suggest certain parameters (e.g., needle length, pressure to be applied by the derma roller 306, etc.).

Figure 3C:
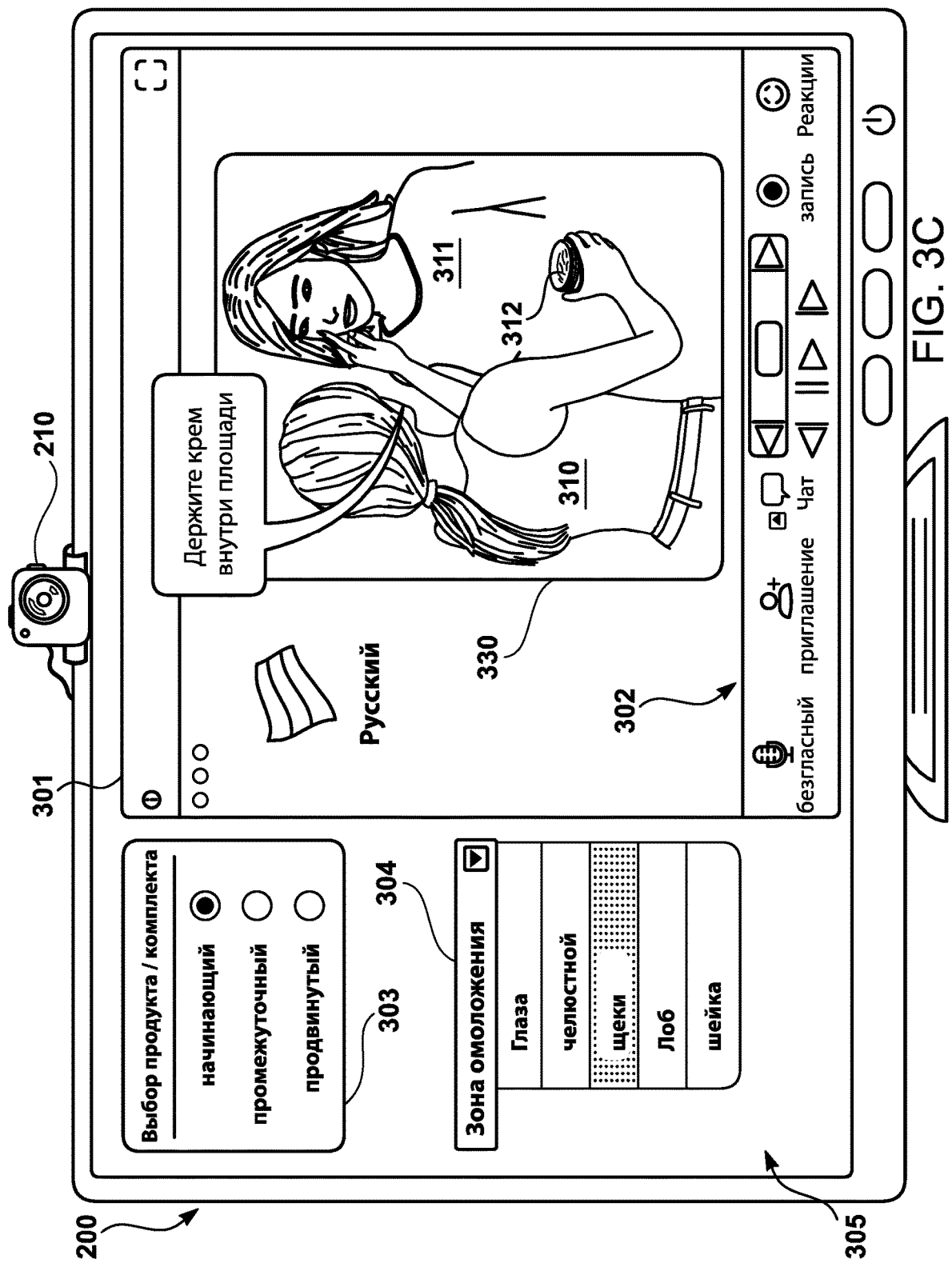
FIG. 3C illustrates an audiovisual window in which the virtual demonstrator demonstrates the second step of the three-step process with Russian-specific content.

The audiovisual window 320 may continue onward in English with respect to the remaining two steps of the three-step process. For the sake of depicting the versatility of the three-step process in spanning multiple languages, FIG. 3C illustrates an audiovisual window 330 in which the virtual demonstrator 310 demonstrates the second step of the three-step process with Russian-specific content. For example, the virtual demonstrator 310 may state, in Russian, "[k]eep the cream inside the square"—referring to utilization of the chemical compound 312 within an area of a predetermined size (e.g., four inches by four inches) in a particular area of intended rejuvenation. Not only is the audio emitted in Russian, but the text displayed for the various controls and menu items also appear in Russian.

Figure 3D:
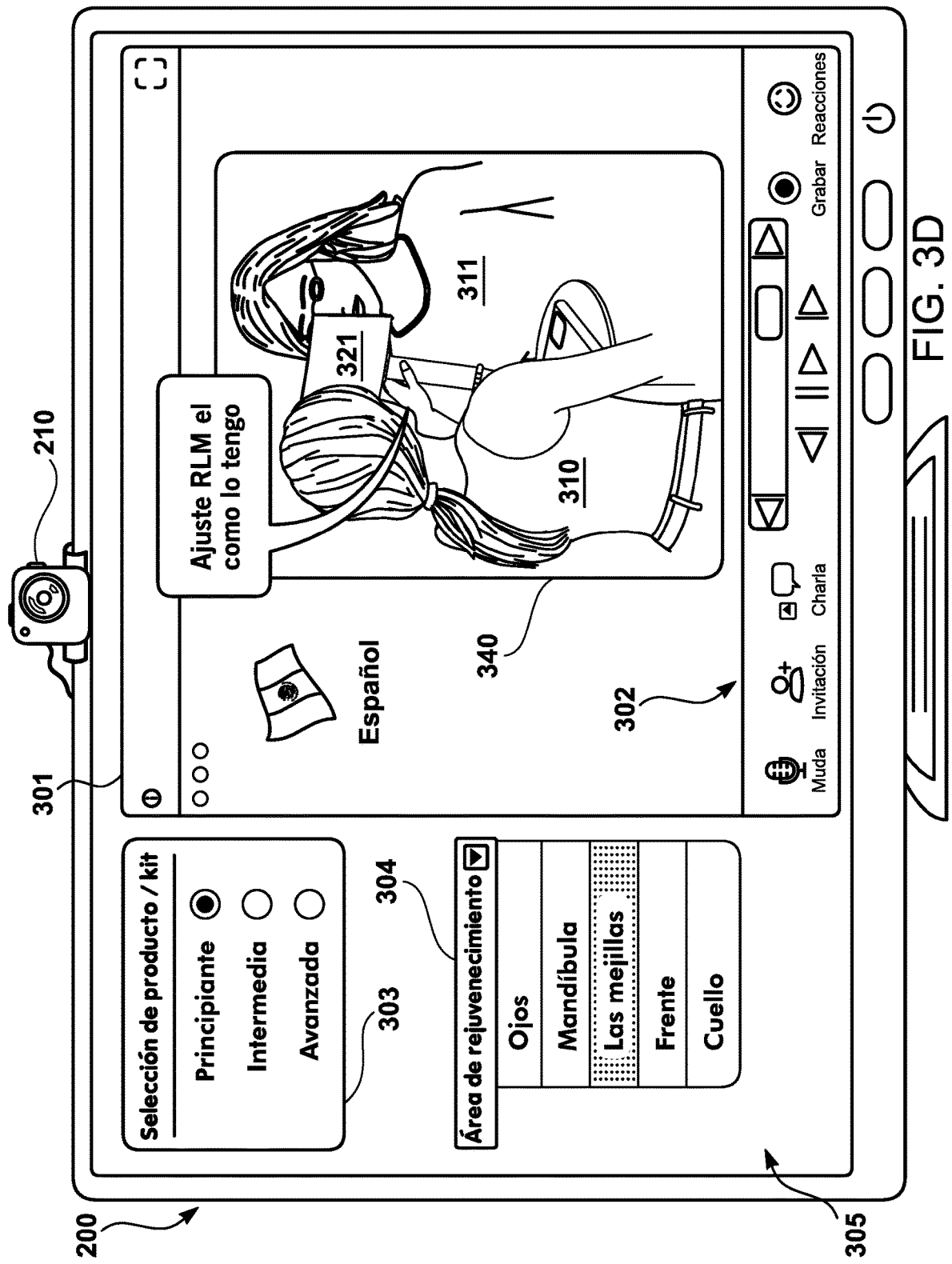
FIG. 3D illustrates an audiovisual window in which the virtual demonstrator demonstrates the third step of the three-step process with Spanish-specific content.

As a final example, which is not intended to be exhaustive given the possibility of the multilingual GUI 201 being utilized for many different languages, FIG. 3D illustrates an audiovisual window 340 in which the virtual demonstrator 310 demonstrates the third step of the three-step process with Spanish-specific content. For example, the virtual demonstrator 310 may state, in Spanish, "[a]djust RLM the way I have it"—referring to utilization of the red light therapy emission device 321 a particular area of intended rejuvenation. Not only is the audio emitted in Russian, but the text displayed for the various controls and menu items also appear in Russian.

Figure 4:
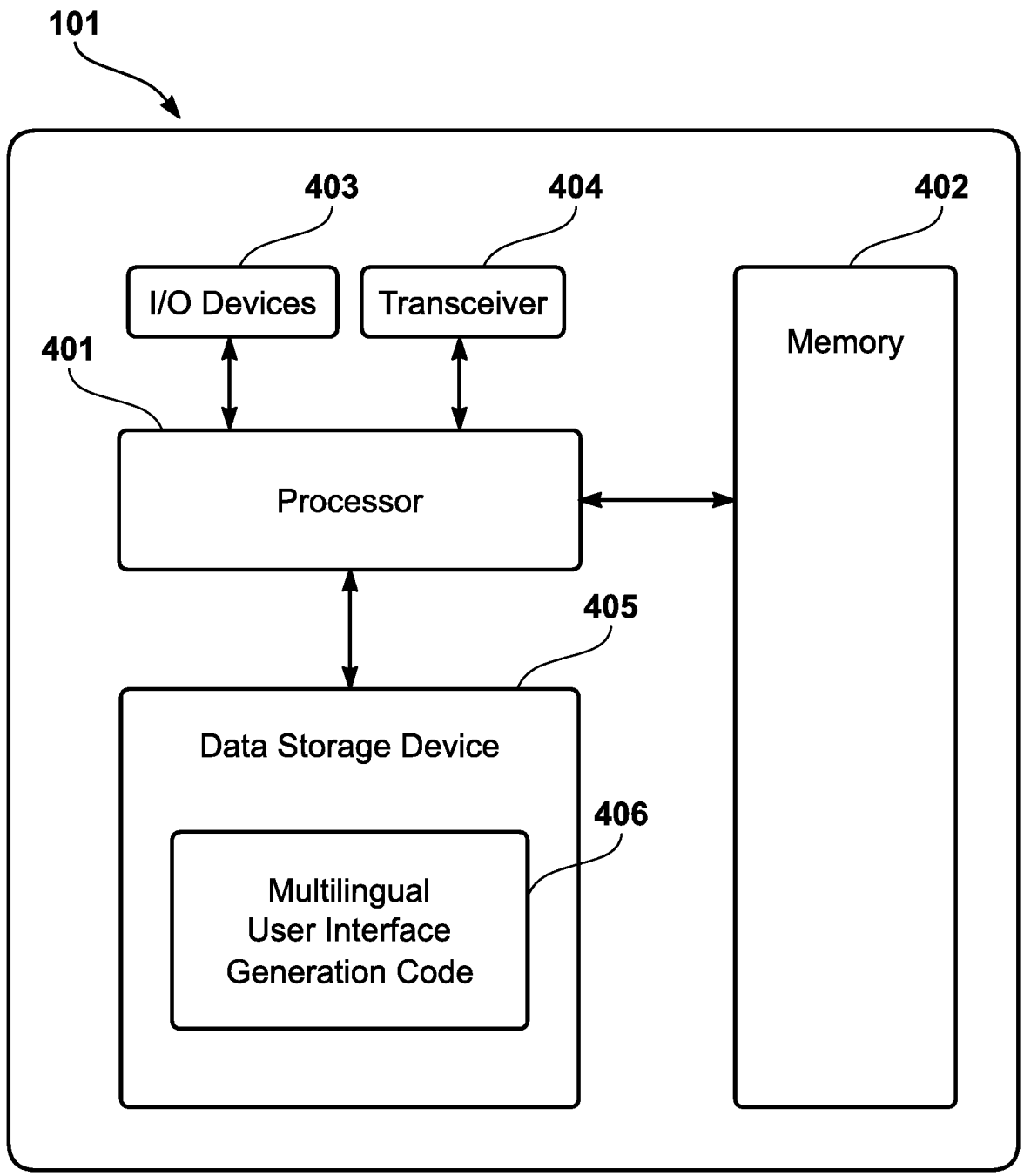
FIG. 4 illustrates a system configuration for the server illustrated in FIG. 1.

FIG. 4 illustrates a system configuration for the server 101 illustrated in FIG. 1. The server 101 may have a processor 401, which may be specialized for multilingual interface generation. Accordingly, the processor 401 may be used to perform the operations illustrated in FIG. 1 for rendering of the multilingual GUI 201 for the three-step skincare treatment process.

The system configuration may also include a memory device 402, which may temporarily store content from one or more of the template database 102, the audiovisual object database 103, and the menu object database 104, illustrated in FIG. 1, for improved processing times by the processor 401. As a result, the multilingual GUI 201 is able to provide real-time (measured as an imperceptible time delay), or substantially real-time (measured as a perceptible time delay that is generally acceptable to the user (e.g., one to two seconds)), audio and/or video instruction for the three-step process via a plurality of virtual platforms. Furthermore, the memory device 402 may store computer readable instructions performed by the processor 401. As an example of such computer readable instructions, a data storage device 405 within the system configuration may store multilingual user interface generation code 406. The processor 401 may execute the multilingual user interface generation code 406 to invoke the multilingual GUI 201.

Moreover, the system configuration may have one or more input/output ("I/O") devices 403 that may receive inputs and provide outputs. Various devices (e.g., image capture devices, keyboard, microphone, mouse, pointing device, hand controller, joystick, display device, holographic projector, etc.) may be used for the I/O devices 403. The system configuration may also have a transceiver 404 to send and receive data. Alternatively, a separate transmitter and receiver may be used instead.

Figure 5:
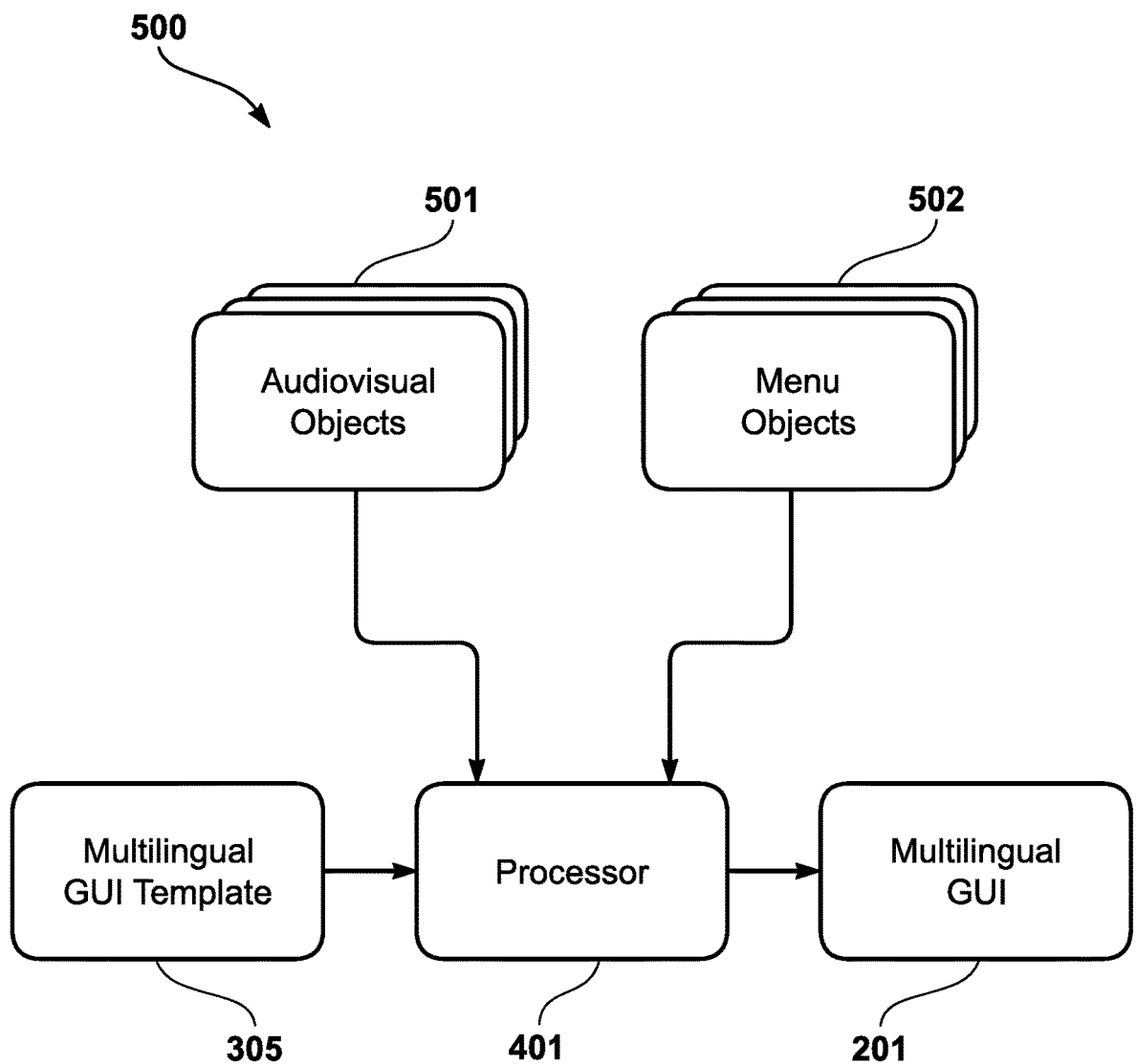
FIG. 5 illustrates a template population configuration that may be utilized by the processor, illustrated in FIG. 4.

FIG. 5 illustrates a template population configuration 500 that may be utilized by the processor 401, illustrated in FIG. 4. In particular, the processor 401 may be a specialized processor that is configured to receive the multilingual GUI template 305 and populate it with one or more audiovisual objects 501 and/or menu objects 502; thereby generating the multilingual GUI 201.

Figure 6:
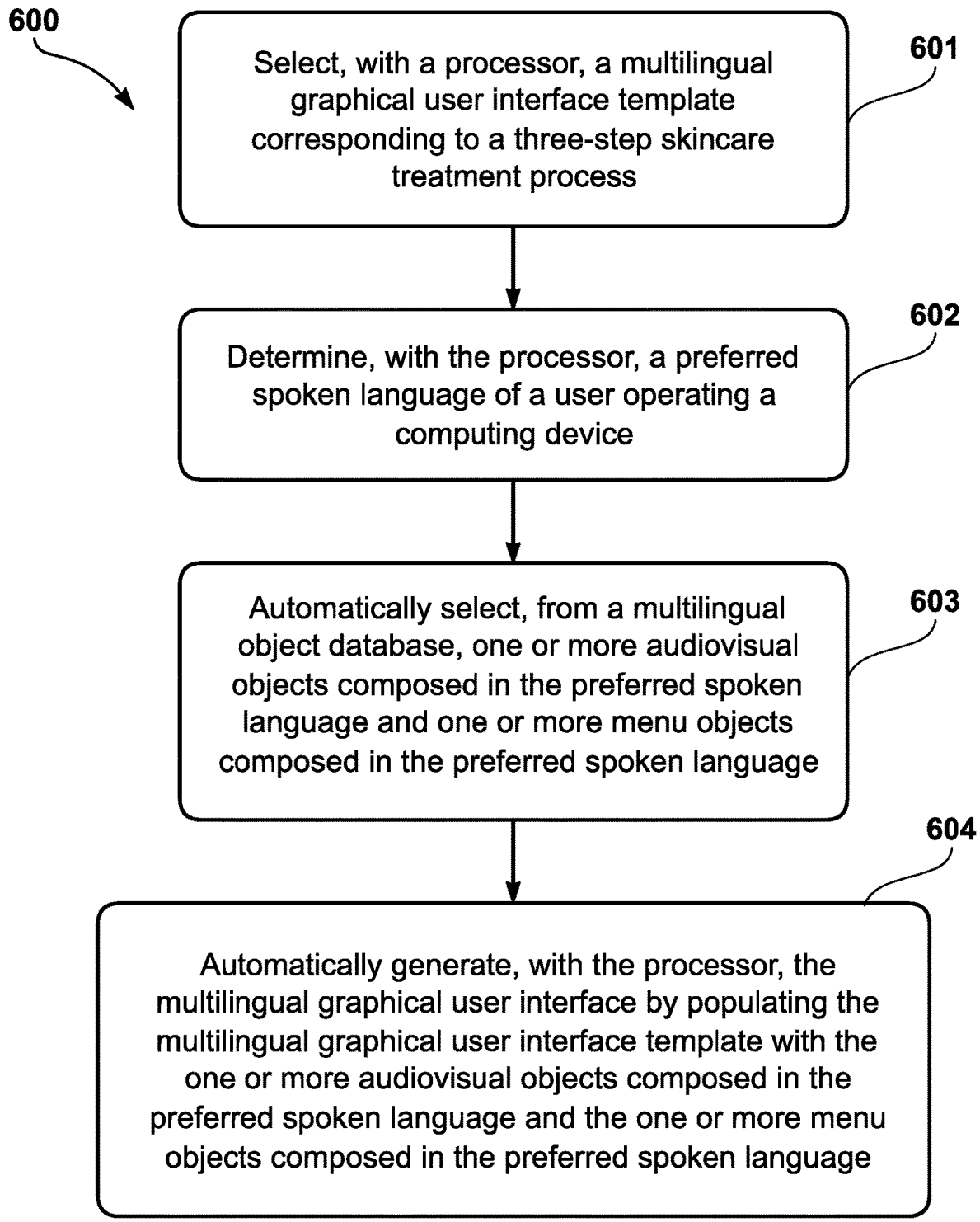
FIG. 6 illustrates a process for generating the multilingual GUI for delivery of the three-step skincare treatment process via one of a plurality of different human spoken languages, as illustrated in FIG. 1.

FIG. 6 illustrates a process for generating the multilingual GUI 201 for delivery of the three-step skincare treatment process via one of a plurality of different human spoken languages, as illustrated in FIG. 1. At a process block 601, the process 600 selects, with the processor 401, the multilingual GUI template 305 corresponding to the three-step skincare treatment process. The multilingual GUI template 305 has a layout of all of the objects present in a multilingual GUI 201 without any, or at least not a substantial portion of, content displaying a human-spoken language. In addition, at a process block 603, the process 600 determines, with the processor 401, a preferred spoken language of a user operating a computing device. Moreover, at a process block 604, the process 600 automatically selects, from a multilingual object database, one or more audiovisual objects composed in the preferred spoken language and one or more menu objects composed in the preferred spoken language. (Alternatively, two different databases, such as the audiovisual object database 103 and the menu object database 104 may be utilized.) Finally, at a process block 605, the process 600 automatically generates, with the processor 401, the multilingual GUI 201 by populating the multilingual GUI template 305 with the one or more audiovisual objects composed in the preferred spoken language and the one or more menu objects composed in the preferred spoken language. The multilingual GUI is configured to render audiovisual content associated with the three-step skincare treatment process.

It is understood that the processes, systems, apparatuses, and computer program products described herein may also be applied in other types of processes, systems, apparatuses, and computer program products. Those skilled in the art will appreciate that the various adaptations and modifications of the embodiments of the processes, systems, apparatuses, and computer program products described herein may be configured without departing from the scope and spirit of the present processes and systems. Therefore, it is to be understood that, within the scope of the appended claims, the present processes, systems, apparatuses, and computer program products may be practiced other than as specifically described herein.

I claim:

1. A computer program product comprising a non-transitory computer readable storage device having a computer readable program stored thereon, wherein the computer readable program when executed on a server computer causes the server computer to:

select, with a processor, a multilingual graphical user interface template corresponding to a three-step skincare treatment process, the multilingual graphical user interface template having a layout of all of the objects present in a multilingual graphical user interface without any content displaying a human-spoken language;

determine, with the processor, a preferred spoken language of a user operating a computing device;

automatically select, from a multilingual object database, one or more audiovisual objects composed in the preferred spoken language and one or more menu objects composed in the preferred spoken language; and automatically generate, with the processor, the multilingual graphical user interface by populating the multilingual graphical user interface template with the one or more audiovisual objects composed in the preferred spoken language and the one or more menu objects composed in the preferred spoken language, the multilingual graphical user interface configured to render audiovisual content associated with a three-step skincare treatment process, the three-step skincare treatment process comprising:

performing, with a derma roller, a predetermined maximum number of movements in each of one or more predetermined directions along an area of intended rejuvenation of a face of a human user, wherein the predetermined maximum number of movements equals four, the derma roller having a head with a plurality of needles each having a length of five tenths millimeters situated thereon, applying, subsequent to the dermal roller performance, a chemical compound to one or more patches of skin at the area of intended rejuvenation, the one or more patches of skin each having a predetermined patch size, the chemical compound comprising vitamin $A_1$, the predetermined patch size equaling four inches in length by four inches in width, and emitting, subsequent to the application of the chemical compound, red light toward the area of intended rejuvenation for a minimum predetermined period of time of ten minutes, the red light having a wavelength in the range of six hundred ten nanometers to seven hundred nanometers.

2. The computer program product of claim 1, wherein the computer is further caused to receive location-based data from a computing device operated by a user of the multilingual graphical user interface, and automatically determine the preferred spoken language of the user based on the location-based data.

3. The computer program product of claim 2, wherein the computer is further caused to generate an introductory screen in the preferred language, and modify the preferred spoken language to a different spoken language based on a user input.

4. The computer program product of claim 1, wherein the computer is further caused to receive a user input from a computing device operated by a user of the multilingual graphical user interface, and automatically determine the preferred spoken language of the user based on the user input.

5. The computer program product of claim 1, wherein the computer is further caused to receive, with the processor, a user input requesting virtual guidance for application of the three-step skincare treatment process via the multilingual graphical user interface.

6. The computer program product of claim 5, wherein the computer is further caused to generate, with the processor, a demonstration window in the multilingual graphical user interface demonstrating the three-step skincare treatment process.

7. The computer program product of claim 6, wherein the demonstration window depicts a human demonstrating the three-step skincare treatment process in the preferred spoken language.

8. The computer program product of claim 6, wherein the demonstration window depicts a computer generated character demonstrating the three-step skincare treatment process in the preferred spoken language.

9. The computer program product of claim 1, wherein the one or more predetermined directions comprise a vertical direction.

10. The computer program product of claim 1, wherein the one or more predetermined movements comprise a diagonal direction.

11. The computer program product of claim 1, wherein the one or more predetermined directions comprise a vertical direction and a diagonal direction to an exclusion of any horizontal direction.

12. The computer program product of claim 1, wherein the performance with the derma roller occurs at a pressure in the range of ten pounds per square inch to fifty pounds per square inch.

13. The computer program product of claim 1, wherein the area of intended rejuvenation is selected from the group consisting of: skin around one or more eyes of the user, skin around one or more cheeks of the user, skin around a forehead of the user, and skin around a jaw of the user.

14. A computer program product comprising a non-transitory computer readable storage device having a computer readable program stored thereon, wherein the computer readable program when executed on a server computer causes the server computer to:

select, with a processor, a multilingual graphical user interface template corresponding to a three-step skincare treatment process, the multilingual graphical user interface template having a layout of all of the objects present in a multilingual graphical user interface without any content displaying a human-spoken language;

determine, with the processor, a preferred spoken language of a user operating a computing device;

automatically select, from a multilingual object database, one or more audiovisual objects composed in the preferred spoken language and one or more menu objects composed in the preferred spoken language;

automatically generate, with the processor, the multilingual graphical user interface by populating the multilingual graphical user interface template with the one or more audiovisual objects composed in the preferred spoken language and the one or more menu objects composed in the preferred spoken language, the multilingual graphical user interface configured to render audiovisual content associated with a three-step skincare treatment process, the three-step skincare treatment process comprising:
- performing, with a derma roller, a plurality of movements along an area of intended rejuvenation of a human user,
- applying, subsequent to the derma roller performance, a chemical compound to one or more patches of skin at the area of intended rejuvenation, and
- emitting, subsequent to the application of the chemical compound, light toward the area of intended rejuvenation;

receive, with the processor, location-based data from a computing device operated by a user of the multilingual graphical user interface; and automatically determine, with the processor, the preferred spoken language of the user based on the location-based data.

15. The computer program product of claim 14, wherein the computer is further caused to generate an introductory screen in the preferred language, and modify the preferred spoken language to a different spoken language based on a user input.

16. The computer program product of claim 14, wherein the computer is further caused to receive a user input from a computing device operated by a user of the multilingual graphical user interface, and automatically determine the preferred spoken language of the user based on the user input.

17. The computer program product of claim 14, wherein the computer is further caused to receive, with the processor, a user input requesting virtual guidance for application of the three-step skincare treatment process via the multilingual graphical user interface.

18. The computer program product of claim 17, wherein the computer is further caused to generate, with the processor, a demonstration window in the multilingual graphical user interface demonstrating the three-step skincare treatment process.

19. The computer program product of claim 18, wherein the demonstration window depicts a human demonstrating the three-step skincare treatment process in the preferred spoken language.

* * * * *